US012131815B2

United States Patent
Bengtsson

(10) Patent No.: US 12,131,815 B2
(45) Date of Patent: Oct. 29, 2024

(54) AUTO LOG-OUT FROM AN EXERCISE MACHINE IN AN EXERCISE MACHINE MONITORING SYSTEM

(71) Applicant: Lumos Holdings US Acquisition Co., Rosemont, IL (US)

(72) Inventor: Henrik Bengtsson, Lund (SE)

(73) Assignee: Lumos Holdings US Acquisition Co., Rosemont, IL (US)

( * ) Notice: Subject to any disclaimer, the term of this patent is extended or adjusted under 35 U.S.C. 154(b) by 765 days.

(21) Appl. No.: 16/969,914

(22) PCT Filed: Apr. 12, 2019

(86) PCT No.: PCT/SE2019/050341
§ 371 (c)(1),
(2) Date: Aug. 13, 2020

(87) PCT Pub. No.: WO2019/212399
PCT Pub. Date: Nov. 7, 2019

(65) Prior Publication Data
US 2021/0125698 A1    Apr. 29, 2021

(30) Foreign Application Priority Data
May 4, 2018  (SE) .................................. 1850532-1

(51) Int. Cl.
*G06F 16/9035*     (2019.01)
*A63B 22/00*       (2006.01)
(Continued)

(52) U.S. Cl.
CPC .......... *G16H 20/30* (2018.01); *A63B 22/0023* (2013.01); *G06F 16/9035* (2019.01);
(Continued)

(58) Field of Classification Search
CPC ........................ G06F 16/9035; A63B 22/0023
See application file for complete search history.

(56) References Cited

U.S. PATENT DOCUMENTS 8,075,453 B1 * 12/2011 Wilkinson ......... A63B 21/4019
482/8
8,683,546 B2 * 3/2014 Dunagan ............... G06F 21/577
726/1
(Continued)

FOREIGN PATENT DOCUMENTS

KR        20170111508 A    10/2017

OTHER PUBLICATIONS

International Search Report and Written Opinion from corresponding International Application No. PCT/SE2019/050341, mailed on Jul. 10, 2019, 10 pages.
(Continued)

*Primary Examiner* — Viral S Lakhia
(74) *Attorney, Agent, or Firm* — Andrus Intellectual Property Law, LLP

(57) ABSTRACT

The invention relates generally to devices, systems (100) and methods for measuring, transmitting, recording and displaying information relating to physical exercise. According to some aspects, the disclosure relates to a method comprising receiving exercise data associated with exercise performed at the exercise machine (1) and associating the received exercise data with a user being logged in at the exercise machine (1). The method further comprises receiving, from a holder (70) arranged at the exercise machine and configured to hold a user device during exercise, a signal indicating an identity of the exercise machine and an indication that an object is removed from the holder, and logging out the user from the exercise machine in response to receiving the signal.

9 Claims, 11 Drawing Sheets

(51) Int. Cl.
  *G16H 20/30* (2018.01)
  *H04W 12/40* (2021.01)
  *H04W 12/47* (2021.01)
  *H04W 12/63* (2021.01)
  *A63B 24/00* (2006.01)

(52) U.S. Cl.
  CPC ......... *H04W 12/47* (2021.01); *A63B 24/0062* (2013.01); *H04W 12/40* (2021.01); *H04W 12/63* (2021.01)

(56) References Cited

U.S. PATENT DOCUMENTS

| | | | |
|---|---|---|---|
| 8,961,371 B2* | 2/2015 | Sultan | G06F 16/2291 |
| | | | 482/901 |
| 9,432,361 B2* | 8/2016 | Mahaffey | H04L 63/0853 |
| 9,474,935 B2* | 10/2016 | Abbondanza | A63B 24/0087 |
| 9,737,759 B2* | 8/2017 | Mrowka | G16H 20/30 |
| 9,763,097 B2* | 9/2017 | Robinson | H04W 12/08 |
| 9,886,557 B2* | 2/2018 | Hsu | G16H 20/30 |
| 10,960,266 B2* | 3/2021 | Messinger | G06V 40/23 |
| 11,383,133 B1* | 7/2022 | Lagree | A63B 22/0023 |
| 11,745,042 B2* | 9/2023 | Bengtsson | A63B 24/0062 |
| | | | 482/8 |
| 2003/0211916 A1 | 11/2003 | Capuano | |
| 2013/0123068 A1* | 5/2013 | Sultan | A63F 13/30 |
| | | | 482/8 |
| 2013/0127636 A1 | 5/2013 | Aryanpur | |
| 2013/0135115 A1* | 5/2013 | Johnson | H04W 56/001 |
| | | | 340/870.02 |
| 2013/0237374 A1* | 9/2013 | Ashby | A63B 71/0054 |
| | | | 482/4 |
| 2015/0012284 A1* | 1/2015 | Schenk | G16H 20/30 |
| | | | 705/2 |
| 2015/0287253 A1 | 10/2015 | Ogata | |
| 2015/0306456 A1 | 10/2015 | Pasini | |
| 2015/0335951 A1 | 11/2015 | Eder | |
| 2016/0346617 A1 | 12/2016 | Srugo | |
| 2017/0106240 A1* | 4/2017 | Chuang | A63B 49/00 |
| 2017/0372055 A1* | 12/2017 | Robinson | H04W 12/64 |
| 2019/0015694 A1 | 1/2019 | Klinghult | |
| 2019/0160335 A1 | 5/2019 | Bentsson | |
| 2019/0286806 A1* | 9/2019 | Robinson | H04L 63/0853 |

OTHER PUBLICATIONS

Swedish Search Report from corresponding Swedish Application No. 1850532-1, mailed on Dec. 3, 2018, 4 pages.

* cited by examiner

AUTO LOG-OUT FROM AN EXERCISE MACHINE IN AN EXERCISE MACHINE MONITORING SYSTEM

TECHNICAL FIELD

The invention relates generally to devices, systems and methods for measuring, transmitting, recording and displaying information relating to physical exercise and, more particularly, to logging out a user from an exercise machine.

BACKGROUND

In recent years, there has been a virtual explosion in the popularity of exercise and physical fitness. There are many popular forms of physical exercise including, for example, running, bicycling, and weight training. The growing interest in weight training is reflected by the growing number of gyms found in both public and private settings.

There are various types of weight training equipment. Typical weight machines, for example, use gravity as the primary source of resistance. A combination of simple machines (e.g., pulleys, levers, wheels, inclines, etc.) to change the mechanical advantage of the overall machine relative to the weight and convey the resistance to the person using the exercise machine. Conventional stacked weight machines, typically include a stack of rectangular weight plates through which a lifting mechanism, e.g. comprising a vertical lifting bar. The lifting bar includes a plurality of holes configured to accept an engaging member, such as a pin. Each of the plates has a corresponding channel that aligns with one of the holes in the lifting bar when the lifting bar is in the lowered or at-rest position. To lift a selected number of the plates, the user operates the engaging member, e.g. by inserting a pin through the channel and the corresponding hole in the lift bar at a selected weight level. As the user goes through the exercise motion, the lift bar rises and the engaging member supports all of the plates stacked above it. The various settings on the weight machine allow the user to select from several different levels of resistance over the same range of motion by simply inserting the pin into the lift bar at a desired weight level.

One important aspect of any type of exercise program is the ability to track personal performance and progress. For example, people engaged in endurance or distance forms of exercise (e.g., running, swimming, bicycling, etc.) often track the distance and/or time associated with a particular run, swim, ride, etc. Similarly, people using cardiovascular exercise machines (e.g., treadmills, stair-steppers, stationary bicycles, etc.) are often interested in knowing how long they exercise or how many calories they burn during a particular session.

One shortcoming of conventional weight machines, however, is that they lack a convenient way for the user to track and record his or her progress on a particular machine or group of machines during a particular exercise session or over a given period of time. As a result, people engaged in weight training programs often rely on memory to keep track of how many weights they lifted on a particular occasion, or how many repetitions they performed on a particular machine. Rather than relying on memory, some people use notebooks to manually record information about their workout. Neither of these approaches, however, is particularly convenient.

In this context, a system for tracking workout related information was suggested in WO2015/113162A1. The system proposed herein includes a bracelet wirelessly connectable to receive workout information related to use of a workout equipment, including a weight being used in the workout equipment. When a user uses a piece of equipment, such as a selectable weight stack machine, the user identifies the equipment to the bracelet, for example by tapping, or otherwise scanning or detecting, an identification tag associated with the equipment. When the bracelet is tapped to the tag, or the tag otherwise read or detected, the exercise equipment identifier may be used in order to establish a wireless communication channel between the equipment and the bracelet. Once the user has completed an exercise the user may move to another piece of equipment to perform a subsequent exercise.

However, if a new user starts exercising at the machine without logging in (by blipping his/her bracelet), the exercise of the new user may be recorded to the previous user. Thus, it may be desirable to provide a way for a user to log out from the machine. One possibility is to let the user again tap, or otherwise scan or detect, the identification tag for the purpose of logging out. However, with such an implementation there is always a risk that the user will forget to log out from the machine.

SUMMARY

An object of embodiments herein is to provide a solutions for automatically logging out users from machines in an exercise monitoring system.

According to a first aspect of embodiments herein it is provided a method for logging out a user from an exercise machine in an exercise machine monitoring system configured to monitor a plurality of exercise machines. The method comprises receiving exercise data associated with exercise performed at the exercise machine and associating the received exercise data with a user being logged in at the exercise machine. The method further comprises receiving, from a holder arranged at the exercise machine and configured to hold a user device during exercise, a signal indicating an identity of the exercise machine and an indication that an object is removed from the holder, and logging out the user from the exercise machine in response to receiving the signal. By using a signal transmitted by a holder, where the user is likely to place a user device during exercise, the user may be automatically logged out from the exercise machine.

According to some embodiments, the method further comprises logging in a user at the exercise machine. According to some embodiments, the logging in is performed in response to receiving a wireless signal indicating the identity of the exercise machine.

According to some embodiments, the method comprises receiving, from the holder, a preceding signal indicating an exercise machine identifier and an indication that an object is placed in the holder. By also providing a preceding signal indicating when an object is placed in the holder, an even more stable solution is achieved.

According to some embodiments, the method is performed simultaneously for a plurality of exercise machines. By using signals transmitted from the holders arranged to the plurality of exercise machines, the exercise monitoring system may keep track of all users in the system.

According to a second aspect of embodiments herein it is provided a method, for use in a holder arranged at an exercise machine and configured to hold a user device during exercise, for assisting an exercise machine monitoring system. The method comprises obtaining sensor data indicating that an object is removed from the holder and sending, to a control arrangement, a signal indicating an identity of the exercise machine and an indication that an object is removed from the holder. The signal enables a receiving control arrangement to log out a user from the exercise machine in response to receiving the signal. The holder is easy to implement and to retrofit in a diversity of already existing systems.

According to some embodiments, the method comprises obtaining sensor data indicating that an object is placed in the holder and sending, to a control arrangement, a preceding signal indicating an identity of the exercise machine and an indication that an object is placed in the holder. By also transmitting a preceding signal makes the solution more robust.

According to a third aspect of embodiments herein it is provided a control arrangement comprises a communication interface configured to enable communication with a plurality of exercise machines each provided with a holder configured to hold a user device of a user during exercise and processing circuitry. The processing circuitry is configured to receive, from one of the exercise machines, exercise data associated with exercise performed at the exercise machine, and to associate the received exercise data with a user being logged in at the exercise machine. The processing circuitry is further configured to receive, from the holder of the exercise machine, an indication that an object is removed from the holder, and to log out the user from the exercise machine in response to receiving the signal.

According to a fourth aspect of embodiments herein it is provided a holder configured to be arranged at an exercise machine to hold a user device during exercise. The holder comprises a sensor and a communication interface. The sensor is configured to sense presence of an object in the holder. The communication interface configured to transmit a signal indicative of the presence to a control arrangement.

According to some embodiments, the proximity sensor is a proximity sensor or a mechanic switch. According to some embodiments, the communication interface is a Bluetooth Low Energy signal.

According to a fifth aspect, an exercise monitoring system is provided, comprising a repetition counter arranged at an exercise machine; a machine identifier configured to transmit a near field wireless signal indicating the identity of the exercise machine; a holder for holding a user's user device during exercise; and the control arrangement (200) in accordance with the mentioned third aspect.

According to some embodiments, the control arrangement of the exercise monitoring system is configured to
receive, from the machine identifier, an identity of the exercise machine and of near field wireless communication with the user device; and, responsive to that receipt,
log in a user of the user device.

In such embodiments, the login and logout procedures are thus different, and suitably arranged for convenient user operation. Login may be performed by the user touching or tapping the machine identifier with the user device, such as holding the user device onto or within a very close proximity to the machine identifier. This provides a clear login procedure for the user. Logout, on the other hand, is simply obtained by subsequently removing the user device from the holder.

In some embodiments, the holder of the exercise monitoring system is configured in accordance with said fourth aspect.

BRIEF DESCRIPTION OF THE DRAWINGS

FIG. 8e illustrates a user interface of a user device.

FIG. 8f illustrates a holder in further detail.

DETAILED DESCRIPTION

Figure 1:
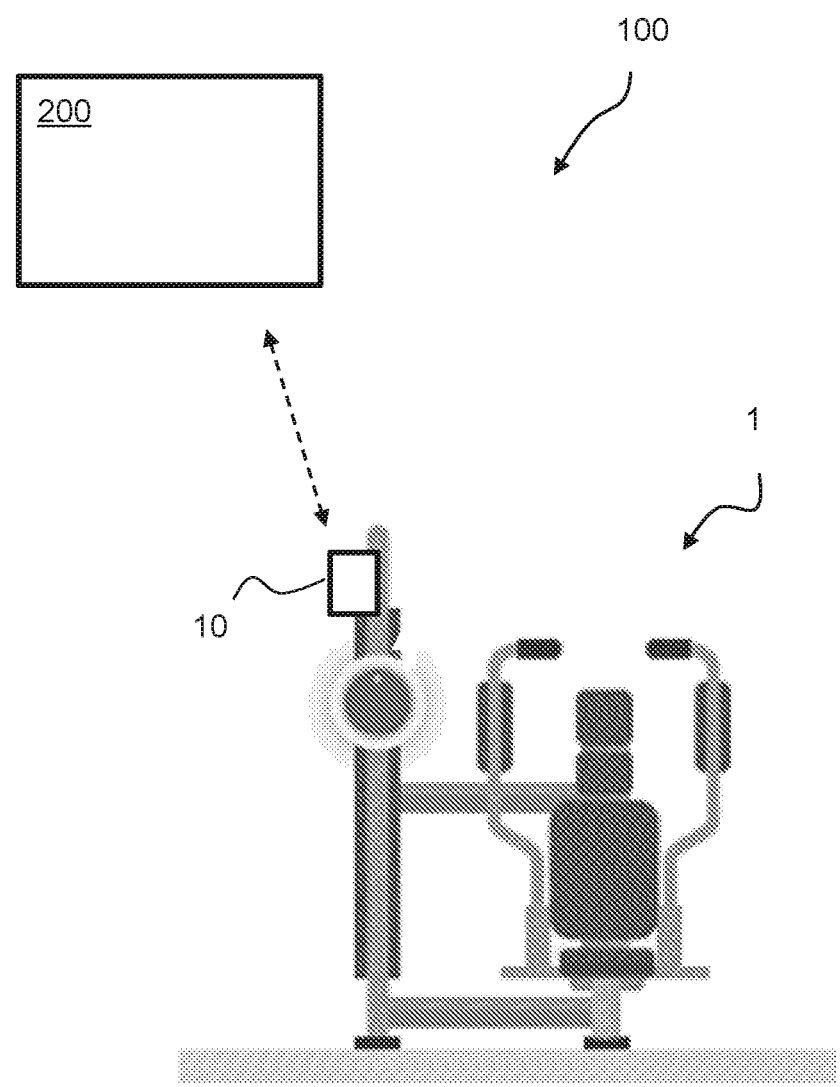
FIG. 1 illustrates an exercise machine monitored by an exercise monitoring system.

Embodiments will now be described with reference to the drawings, wherein like reference numerals are used to refer to like elements throughout.

FIG. 1 illustrates an exercise machine 1 arranged to be monitored by an exercise monitoring system 100. The exercise monitoring system 100 comprises a repetition counter 10 and a control arrangement 200. The repetition counter 10 is arranged to the exercise machine 1 and is configured to collect data associated with exercise performed at the exercise machine 1. For example, the repetition counter 10 is configured to count the number of repetitions performed by a user. The repetition counter 10 may also obtain other information such as weight lifted.

The control arrangement 200 is configured to control the monitoring of the exercise machine 1. The control arrangement 200 comprises one or more parts or devices. The one or more devices typically includes at least a backend server. The control arrangement 200 may also include one or more user devices, e.g. smartphones or similar. In other words, the control functionality may be distributed between several physical units. Thus, the control arrangement 200 is in some embodiments a physical backend server and in some embodiments a functional unit implemented in several physical devices, as further illustrated in FIGS. 7 and 10.

The control arrangement 200 is configured to receive exercise data from the repetition counter 10, to store the received data and analyze the received data and to provide relevant information to e.g. the user and/or the gym owner. The user may e.g. receive information about the exercise in a user device such as a smartphone. The user may then track his/her exercise in real-time in his user device. For example, an exercise application in the user device may display number of repetitions performed in real-time.

As described above, the control arrangement 200 typically monitors a plurality of users and exercise machines 1 in parallel i.e. (essentially) simultaneously. Hence, the control arrangement 200 needs to keep track of which user is performing exercise in a particular exercise machine 1. As mentioned above, this may be accomplished by letting the user tap a user device to a "tag" associated with the exercise machine 1.

It is herein proposed to improve this functionality by adding an automatic "log-off" feature, implemented in holders arranged to the exercise machines. The holder is e.g. a holder where the user can put his or her user device while performing exercise. The holder is typically arranged and configured such that a user is able to view the display of the user device. For example, it is made of a transparent material. It is assumed that a user that uses a user device such as a smartphone to monitor his or her exercise in real-time would be likely to place his smartphone in the holder in order to be able to view the display of the smartphone while exercising.

Figure 2:
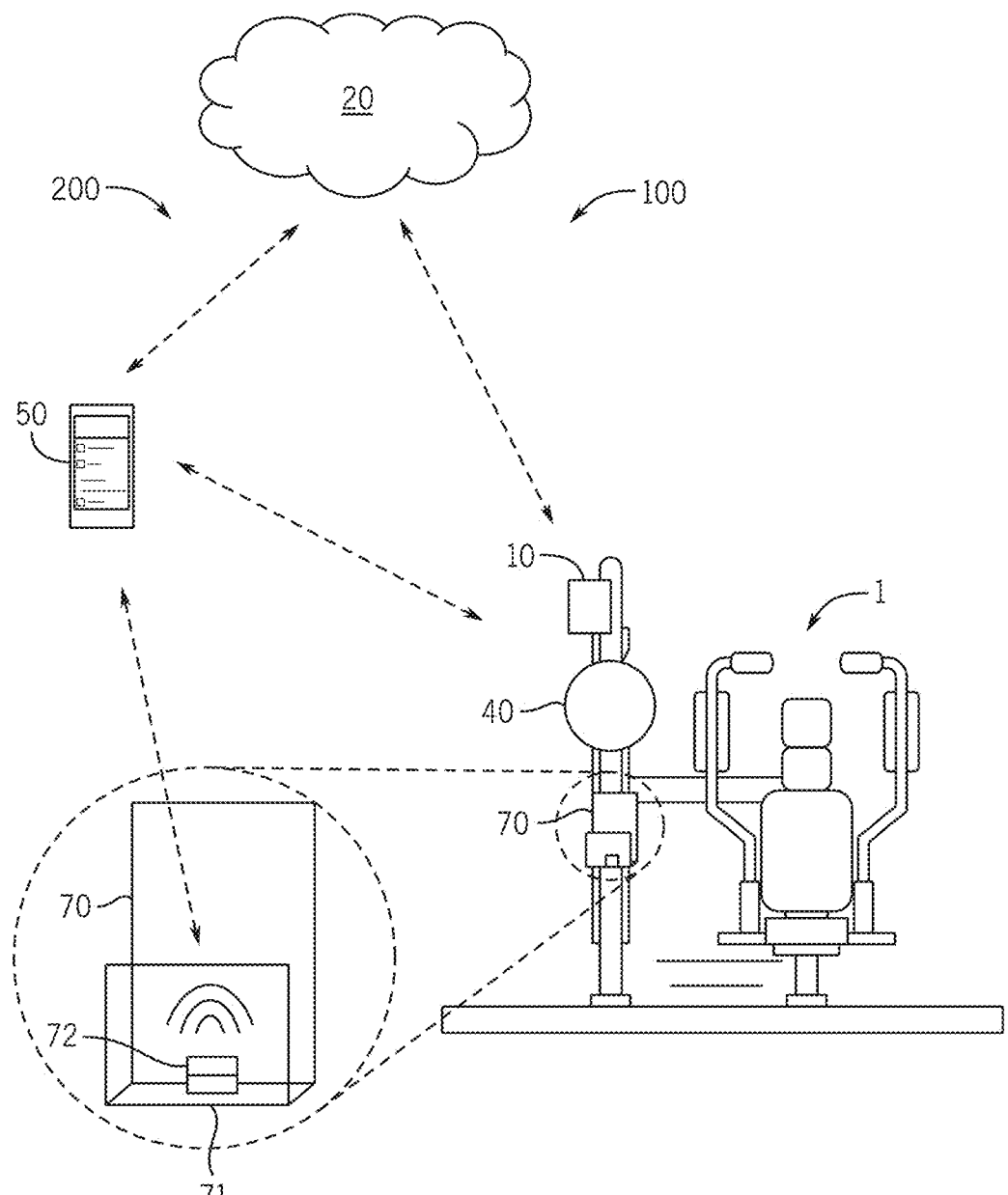
FIG. 2 illustrates an exercise monitoring system comprising a holder configured to enable logging out a user from the monitoring system.

FIG. 2 illustrates an exercise monitoring system 100 configured to enable logging out a user from the monitoring system 100 in more detail. In addition to the repetition counter 10 and the control arrangement 200, the exercise monitoring system 100 comprises an exercise machine identifier 40 and a holder 70 for holding a user's user device 50 during exercise.

The repetition counter 10 is described in detail below in connection with FIGS. 7 and 8a.

The exercise machine identifier 40, also referred to as a simply a "puck", is configured to transmit a near field wireless signal indicating the identity of the exercise machine. The signal is e.g. NFC or RFID. The signal is for example received by the user device 50 (e.g. a user's smartphone). The user device 50 may then log in at exercise machine 1, e.g. inform the server 20 that he/she intends to start exercising in the exercise machine 1. This may be accomplished in different ways. Some example embodiments will be described in connection with FIG. 7 to FIG. 11.

The holder 70 is a holder suitable to hold a user device 50 such as a smartphone or a tablet. The holder 70 is configured to be arranged at an exercise machine 1 to hold a user device during exercise. It is preferably arranged such that a user can watch a display of a user device 50 placed in the holder 70 when performing exercise. The holder 70 comprises a sensor 71 and a communication interface 72. In some embodiments, the holder 70 comprises additional hardware such as a microprocessor and/or a physical connector configured to be connected to a user device.

The sensor 71 is configured to sense presence of an object in the holder 70. In some embodiments the sensor 71 is a simple device such as a proximity sensor or a mechanical switch. Such a sensor 71 may not detect that the object is actually a user device. However, if the shape of the holder is configured e.g. to receive a smartphone, then it may be assumed that the object is a smartphone. If the user places another personal object (e.g. a note book) in the holder during exercise, the proposed technique would anyhow work, as the user would also in this case typically remove the object when leaving the exercise machine 1 after completing the exercise. The sensor may alternatively be a more complex device that e.g. establishes a connection with the user device 50 and verifies that the object is a user device 50.

The communication interface 72 is a wireless interface configured to transmit a wireless signal (e.g. a short-range wireless signal) indicative of the presence to a control arrangement 20. The transmission is e.g. a broadcast transmission that can be received by any compliant device, i.e. not only the user device 50 of the present user. The communication interface 72 is for example a Bluetooth Low Energy interface.

In this example the control of the exercise monitoring (i.e. the control arrangement 200) is implemented in a server 20 (backend) and a user device 50 (frontend). The control arrangement 200 is configured to receive, analyze and distribute exercise data associated with exercise performed at the exercise machine 1 and associate the received exercise data with a user being logged in at the exercise machine. The control arrangement 200 is further configured to perform the proposed method for logging out a user from the exercise machine that will now be further described with reference to FIG. 3 and FIG. 4.

Figure 3A:
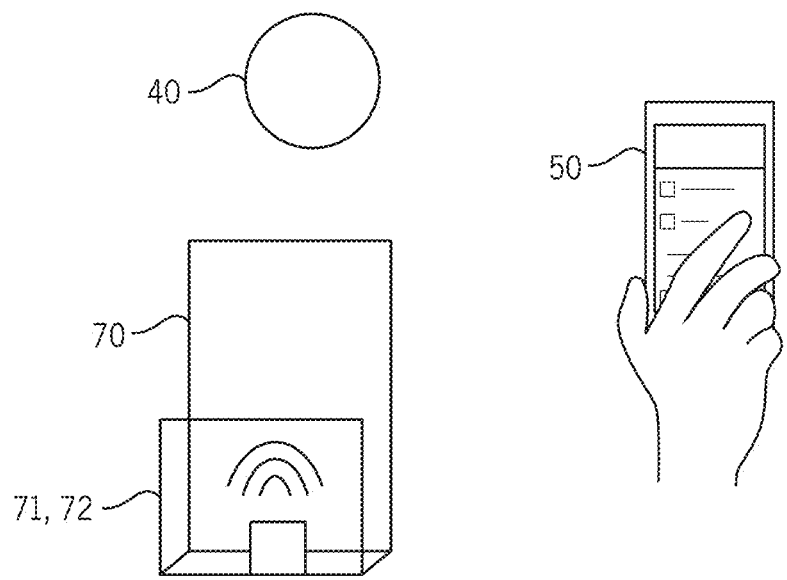
FIG. 3a-FIG. 3d illustrates the procedure for logging in and logging out the user from the exercise monitoring system.
Figure 3B:
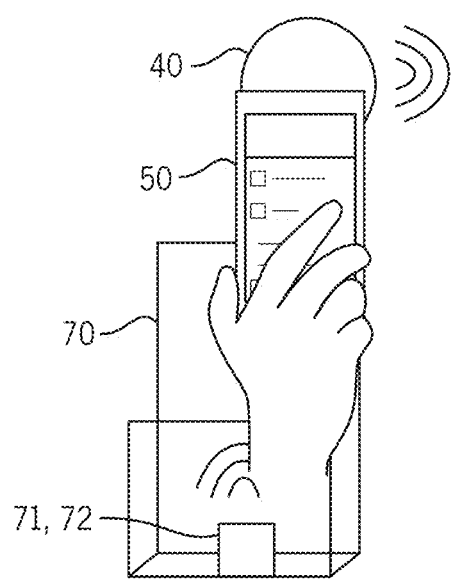
Figure 3C:
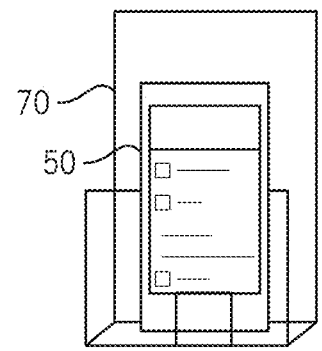
Figure 3D:
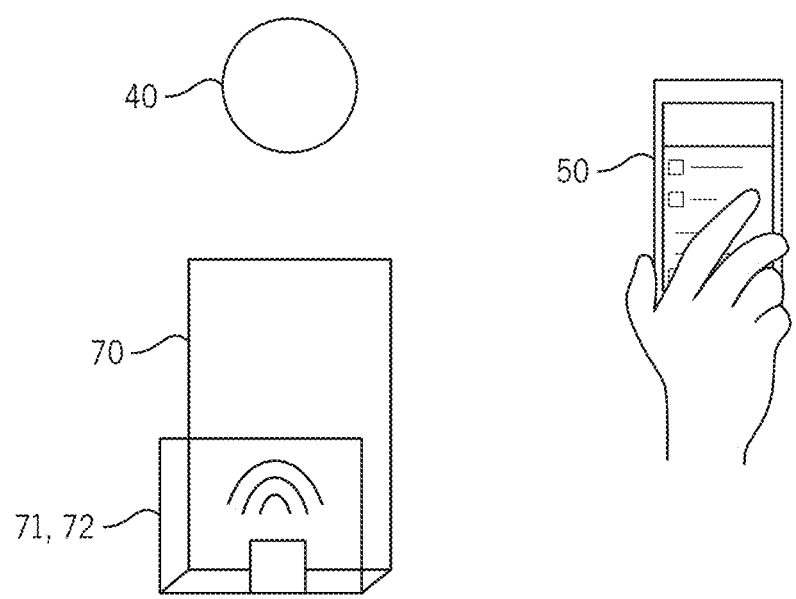

FIGS. 3a to 3d illustrates the concept of logging in and logging out a user from the exercise monitoring system 100 of FIG. 2. In FIG. 3a a user holds a user device 50 (here a smartphone) in his hand. The user intends to start exercise at the exercise machine 1. In FIG. 3b the user blips (or taps) the exercise machine identifier 40, whereby the user is logged into the exercise machine 1. In FIG. 3c the user device is put in the holder 70. The user then performs his exercise. During the exercise the user watches the screen of the user device 50, which displays exercise information. The user may e.g. in real-time monitor the number of repetitions performed. Other information such as speed and weight might also be shown. For example, information regarding whether the speed is too high or too low is provided. When the user is finished, the user device 50 is taken out from the holder 70, as illustrated in FIG. 3d, whereby the user is logged out from the exercise machine 1.

Figure 4:
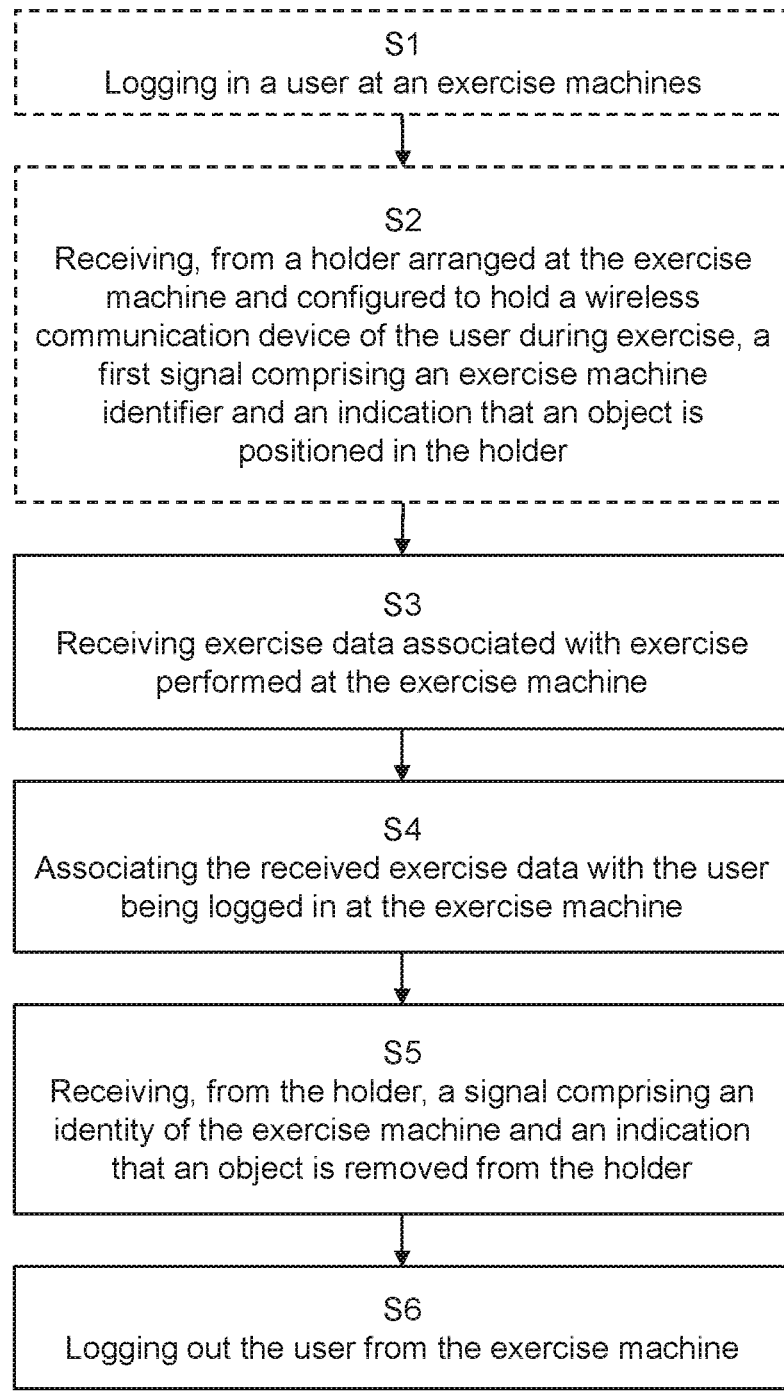
FIG. 4 illustrates a method for use in a control arrangement of the exercise monitoring system according to some embodiments.

FIG. 4 illustrates operations performed in the control arrangement 200 of the exercise monitoring system 100 for logging out a user from an exercise machine 1. The method may be implemented as a computer program comprising instructions which, when the program is executed by a computer, cause the computer to carry out the method. According to some embodiments the computer program is stored in a computer-readable medium (e.g. a memory or a compact disc) that comprises instructions which, when executed by a computer, cause the computer to carry out the method. The method may be performed at any time when a user is logged in at an exercise machine 1.

In some embodiments, the method comprises the actual step of logging in S1 the user at the exercise machine. The logging in S1 is for example performed in response to receiving a near-field wireless signal comprising (or being indicative of) the identity of the exercise machine. For example, a near-filed communication signal transmitted by the exercise machine identifier 40 is received by the user device 50. The user device then sends a message to the server 20 informing the server about the identity of the user (e.g. the identity of the user device 50) and the exercise machine 1, to which the user is logged in. That the user is logged or registered at the exercise machine 1 means that there is an association between the user and the exercise machine 1, e.g. in the server 20.

In some embodiments, the method further comprises receiving S2, from the holder 70, a first wireless signal (e.g. a short-range wireless signal) comprising an exercise machine identity and an indication that an object is placed in the holder 70. For example, the user device 50 receives a Bluetooth Low Energy, BLE, signal from the holder 70. In general, the proposed method works, by simply using a signal which is transmitted every time an object is removed from the holder 70. However, to also signal that an object, which is assumed to be a user device 50, is placed in the holder 70 will make the system more stable. Such a signal may trigger the control arrangement 200 to scan for a succeeding wireless signal indicating that an object is removed from the holder 70. Furthermore, a second wireless signal indicating that an object is removed from the holder 70 may be ignored if not succeeded by a further signal comprising (or being indicative of) an exercise machine identity and an indication that an object is placed in the holder 70.

The method comprises receiving S3 exercise data associated with exercise performed at the exercise machine 1. For example, information about number of repetitions and weight lifted at a particular machine is received from the exercise machine 1 (e.g. from the repetition counter). The exercise data may be received by the user device 50 and/or by the server 20. The exercise data may be forwarded to the control arrangement 200 via other devices in the exercise monitoring system 100 that are configured to collect and forward exercise data, as will be further explained in FIG. 7.

It must be appreciated that in reality the exercise machine monitoring system 100 will monitor a plurality of exercise machines, e.g. all machines in a gym. Then the control arrangement 200 will receive exercise data for a plurality of exercise machines 1 and signals from a plurality of holders 70. Thus, in some embodiments, the method is performed in parallel or (essentially) simultaneously for a plurality of exercise machines 1.

The method further comprises associating S4 the received exercise data (for the particular exercise machine 1) with a user being logged in at the exercise machine 1. The associating e.g. implies that the exercise data is stored in a database (e.g. in the server 20 or in the user device 50), in a way such that it is clear which user performed the exercise. The association between the user and the exercise machine, enables the control arrangement to store the exercise data in connection with a particular user, e.g. in the user's user account in the server 20 or in the user device of the user. If the exercise data is received by the user device 50 of the user, then information about the exercise may be displayed to the user in real-time.

The method further comprises receiving S5, from a holder 70 arranged at the exercise machine and configured to hold a user device 50 of a user during exercise, a wireless signal (e.g. a short-range wireless signal) comprising (or indicating) an identity of the exercise machine and an indication that an object is removed from the holder 70.

The method further comprises logging out S6 the user from the exercise machine 1 in response to receiving the signal. When receiving the signal, the control arrangement 200 checks which user (or possibly users) is logged in at the exercise machine 1 and logs out the user (or users), i.e. removes the association between the exercise machine 1 and the user.

Figure 5:
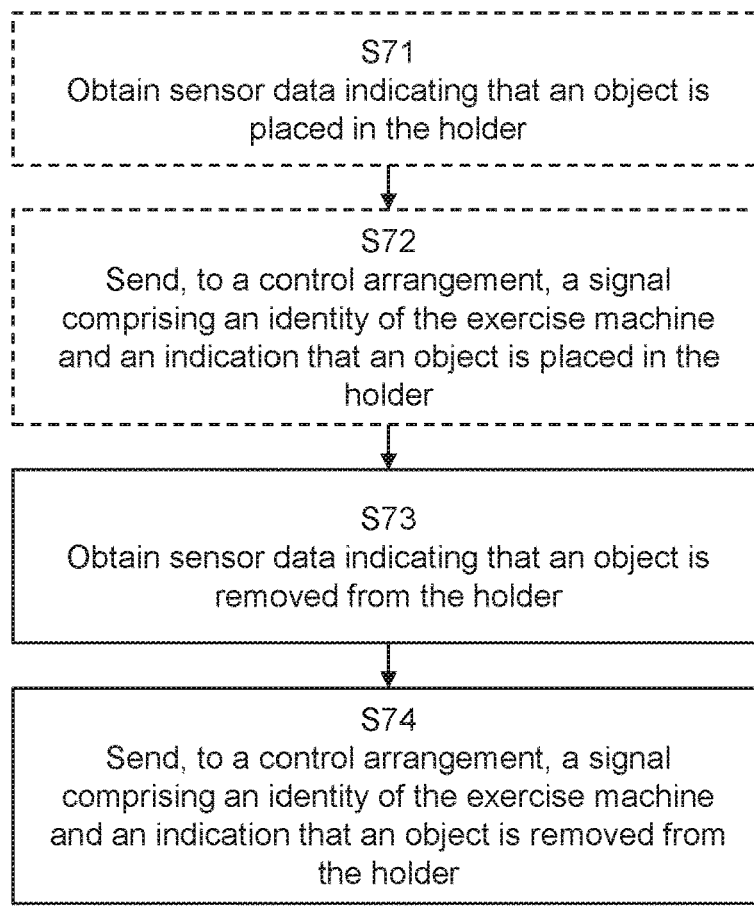
FIG. 5 illustrates a method for use in a holder of the exercise monitoring system according to some embodiments.

FIG. 5 illustrates operations performed in the holder 70 for assisting an exercise machine monitoring system 100 in logging out a user. The method is e.g.

performed in the holder 70 of FIG. 2.

The method comprises obtaining S73 sensor data S12 indicating that an object is removed from the holder 70. For example a proximity sensor 71 detects that an object that was in proximity of the sensor 71 is not any longer in proximity. The proximity sensor 71 e.g. generates a sensor signal that indicates the proximity of an object. The method further comprises sending S74, to a control arrangement 200, a wireless signal (e.g. a short-range wireless signal) comprising an identity of the exercise machine and an indication that the object is removed from the holder 70. For example, a wireless communication interface receives the sensor signal from the proximity sensor 71 and, in response to receiving the sensor signal, transmits the wireless signal.

As mentioned above, the signal indicating removal of an object may a second signal, which is preceded by a first signal (herein referred to as a further signal) indicating than an object is placed in (or present in) the holder. In other words, in some embodiments, the method comprises obtaining S71 sensor data S10 indicating that the object is placed in the holder 70 and sending S72, to a control arrangement 200, a further wireless signal comprising (or being indicative of) the identity of the exercise machine and an indication that the object is placed in the holder 70. For example a proximity sensor 71 detects that an object is positioned (or placed) in proximity of the sensor 71. The proximity sensor 71 e.g. generates a sensor signal that indicates the proximity of an object. The wireless communication interface receives the sensor signal from the proximity sensor 71 and, in response to receiving the sensor signal, transmits the further wireless signal.

Figure 6:
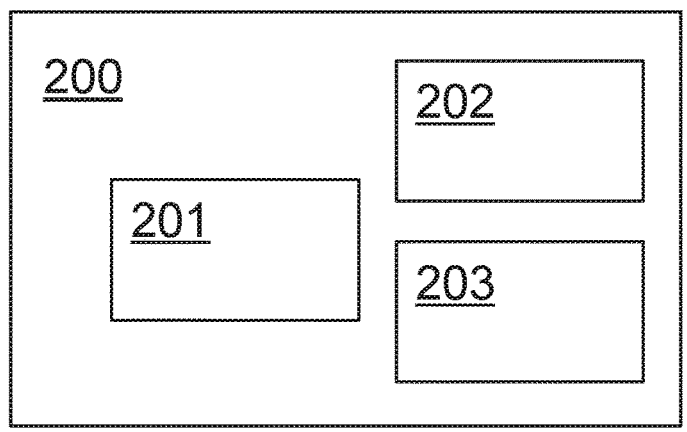
FIG. 6 illustrates a control arrangement according to some embodiments.

FIG. 6 illustrates a control arrangement 200 according to some embodiments. The control arrangement 200 comprises a communication interface 201 and processing circuitry 202. As mentioned above, the control functionality of the exercise machine monitoring system 100 (i.e. the control arrangement 200) may be distributed between a plurality of devices. Hence, the communication interface 201 and processing circuitry 202 are in some embodiments implemented as a plurality of communication interfaces and processing circuitries.

The communication interface 201 is configured to enable communication with a plurality of exercise machines each provided with a holder configured to hold a user device of a user during exercise. The communication interface 201 is in some embodiments configured to enable communication within the control arrangement e.g. between a server 20 and a user equipment 50. The communication interface 50 may be wireless ore wired (or a combination thereof). The communication uses one or several different communication protocols e.g. Bluetooth Low Energy for communication with the holder 70 and the exercise machines 1 and WiFi for communication with a backend server 20.

The processing circuitry 202 is e.g. a processor or a microprocessor or a combination thereof. The processing circuitry 202 is configured to cause the control arrangement 200 to receive, from one of the exercise machines 1, exercise data associated with exercise performed at the exercise machine 1 and associate the received exercise data with a user being logged in at the exercise machine 1. For example, exercise data is collected and stored in a server 20 (FIG. 2). The processing circuitry 202 is further configured to cause the control arrangement 200 to receive (e.g. using the communication interface 201), from the holder 70 of the exercise machine 1, an identity of the exercise machine and an indication that an object is removed from the holder 70.

The control arrangement 202 is further configured to log out the user from the exercise machine 1 in response to receiving the wireless signal. This e.g. corresponds to removing an association between the user and the exercise machine 1 stored in a memory 203 of the control arrangement 200.

Figure 7:
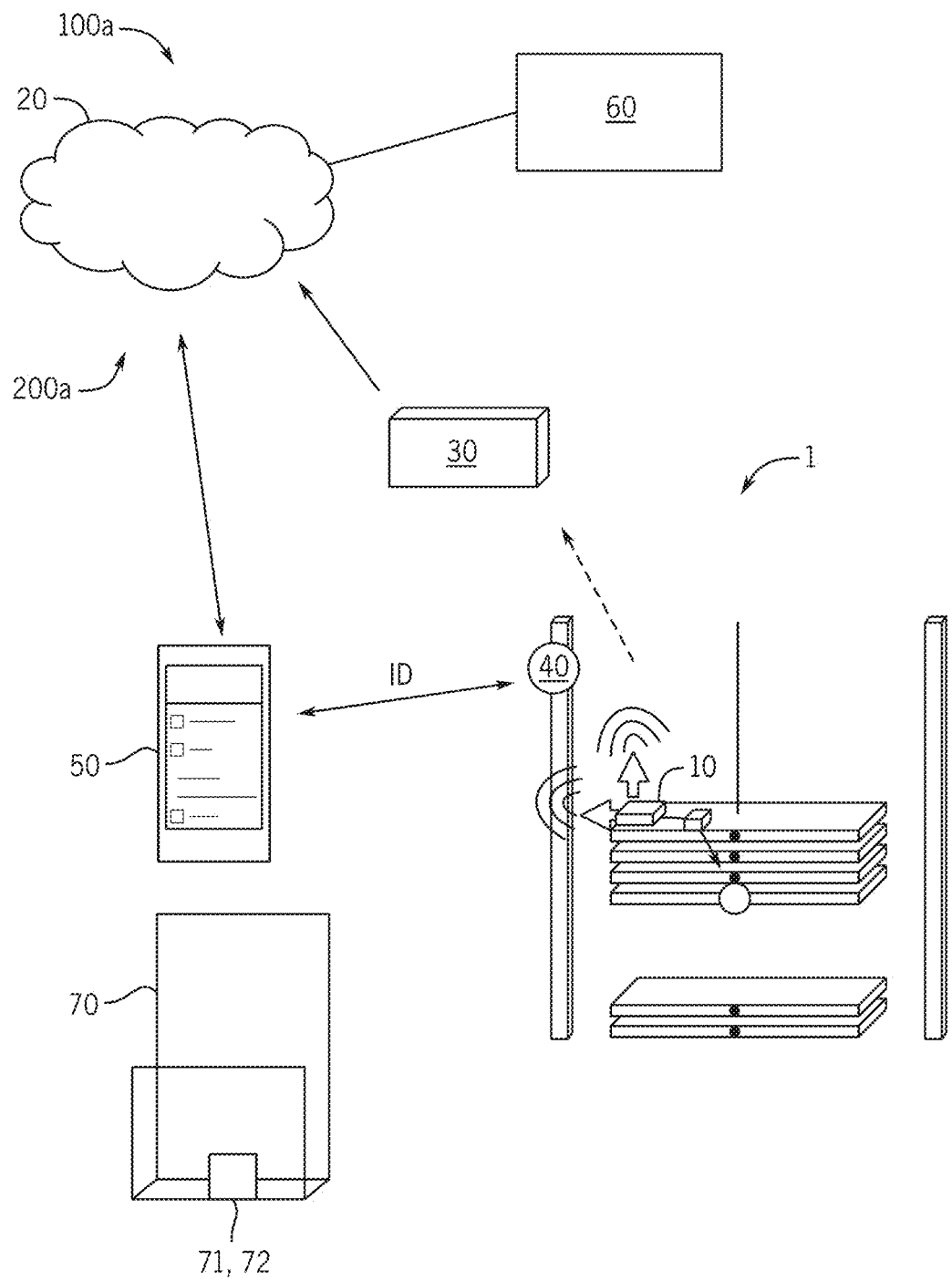
FIG. 7 illustrates an example exercise monitoring system.

FIG. 7 illustrates an exercise monitoring system where the proposed technique may be implemented.

A first example implementation of the proposed technique is shown in FIG. 7. In this example only one exercise machine 1 is shown. However, it must be appreciated that the monitoring system would typically be arranged to monitor a plurality of exercise machines. FIG. 7 illustrates an exercise machine monitoring system 100a comprising one repetition detector 10, one exercise machine identifier 40 and a holder 70 for each exercise machine that is to be monitored. The monitoring system 100 further comprises a server 20, at least one observer 30, and a user device 50. The server has access to a data storage 60.

Figure 8A:
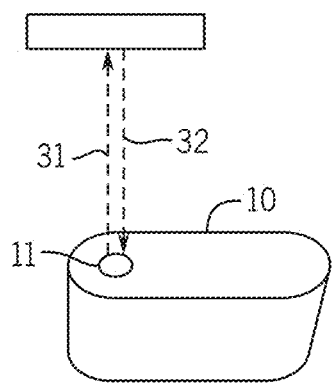
FIG. 8a illustrates a repetition counter in further detail.
Figure 8B:
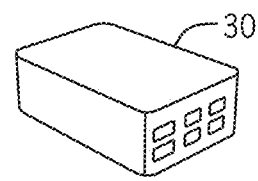
FIG. 8b illustrates an observer in further detail.
Figure 8C:
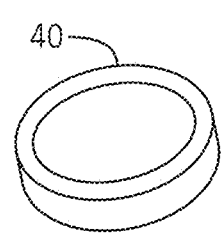
FIG. 8c illustrates an exercise machine identifier in further detail.

FIG. 8a shows the repetition detector 10, also referred to as a main unit, in further detail. The repetition detector 10 is configured to be arranged to the stacked weights 2 of exercise machine 1. For example it is configured to be arranged on the top of the stack of weights i.e. on the uppermost weight (FIG. 7).

The repetition detector 10 advertises information (e.g. a series of integers) associated with the exercising using short range wireless communication.

More specifically, the repetition detector 10 comprises a sensor arrangement 11 configured to provide sensor data indicative of a longitudinal movement of at least some of the stacked weights 2. In other words, the repetition detector 10 comprises a sensor arrangement 11 configured to detect when a user performs an exercise in the exercise machine 1, by detecting longitudinal movements (herein also referred to as repetitions) of at least some of the stacked weights 2. The sensor arrangement 11 may e.g. comprise an accelerometer, range finder, a tension meter and/or similar. In an example implementation the sensor arrangement 11 comprises a light range finder. The light range finder is configured to transmit a laser beam 31 and to receive a reflection 32 of the transmitted laser beam to determine the distance to a fixed point of the upper part of the exercise machine. For example, the rangefinder operates on the time of flight principle by sending a laser pulse in a narrow beam towards the object and measuring the time taken by the pulse to be reflected off the target and returned to the sender.

Detection of a longitudinal movement of the stacked weight would then typically correspond to detecting that the distance between the repetition detector 10 and the exercise machine has changes a pre-determined amount, which corresponds to that the stacked weights 2 lave been lifted. It is also possible to detect that at least some of the stacked weights 2 have moved more than a pre-determined distance upwards and then starts moving in the opposite direction.

The repetition detector 10 further comprises a short range wireless communication interface. The short range wireless communication interface e.g. uses Bluetooth Low Energy, BLE, ZigBee, LoRa.

The repetition detector 10 further comprises control circuitry configured to detect a longitudinal movement based on the sensor data provided by the sensor arrangement 11. The control circuitry is further configured to broadcast, using the short range wireless communication interface, a signal (i.e. an advertisement) comprising an identity of the exercise machine 1 and an indication of the detected longitudinal movement of at least some of the stacked weights 2. The broadcasted signal comprise may also comprise other data such as a sequence number and/or repetition number or other information.

For this type of applications low power consumption is crucial. Thus, in some embodiments the control circuitry is also configured to implement a power control function. The repetition detector 10 is then set in a sleep mode (which corresponds to practically completely switched off) when no exercise is performed, i.e. when the repetition detector 10 (and the stacked weights 2) are not moving. An accelerometer or similar is then used to wake-up the repetition detector 10 when it starts moving. The sensor arrangement 11 is then activated and starts detecting repetitions. If the repetition detector 10 is still for more than a few seconds it will return to sleep mode.

The detection and broadcasting is typically performed in real-time, such that each and every repetition that a user performs in the exercise machine is "reported". Thus, it is important that each and every signal can be correctly observed. Therefore, in one example implementation the broadcasted signal comprises a pulse-train of ten repeated signals.

In some embodiments, the repetition detector 10 also comprises or is connected to a weight sensing device. The weight sensing device is configured to estimate the weight that the user uses when training. This may e.g. be implemented by measuring a distance between the weight sensing device and an engaging member. One example implementation is shown in international patent application WO2017/178048. Then the broadcasted signal also comprises information about the estimated weight.

In conclusion, the at least one repetition detector 10 is configured to broadcast a short range wireless signal comprising (or being indicative of) an identity of the exercise machine 1 and an indication of a longitudinal movement of at least some of the stacked weights 2.

The exercise machine identifier 40, also referred to as a puck (FIG. 8c), corresponds to the exercise machine identifier 40 described in connection with FIG. 2.

Figure 8D:
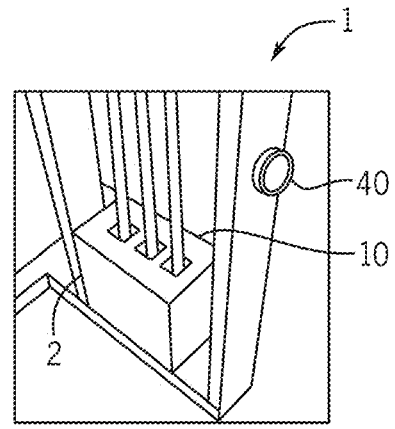
FIG. 8d illustrates the exercise machine identifier and the repetition detector when mounted.

FIG. 8d illustrates the exercise machine identifier 40 and the repetition detector 10 when installed in the exercise machine 1. The repetition detector 10 is then mounted in the upper weight of the stacked weights 2.

The observer 30 (FIG. 8b) comprises a short range wireless communication interface, for monitoring short range wireless signals transmitted by repetition detectors 10 arranged to a plurality of exercise machines in a gym. The observer 30 is configured to receive signals broadcasted by repetition detectors 10 and to generate exercise data based on the received signals. More specifically the observer 30 parses the data from the advertisement (e.g. a series of integers), and sends it on the server 20. The observer 30 typically doesn't know whether a user is registered or logged in at the machines, it just sends all correctly parsed advertisements. This means that all training in the gym is tracked, even when the user is not registered to the service. More specifically, when the observer receives a pulse train from the repetition detector 10, then it filters the repetitions, e.g. removing duplicates having the same repetition number, and interprets it as one repetition. The generated exercise data is then forwarded to the server 20, where it is typically for stored in the data storage 21. The observer 30 e.g. uses ordinary internet communication for communication with the server 20.

The data storage 21 is configured to store the exercise data of the exercise machines. In this embodiment the data storage 21 is comprised in a server 20 or backend. Thus the data storage 21 is e.g. a cloud implemented database or a remote database. The data stored in the data storage 21 may be used to gain insights and data about gym members and their training patterns and would also enable detailed analysis of utilization of gym machines.

The server 20 typically communicates over internet i.e. using IP/Ethernet. The server 20 will receive exercise data from the observer and store it in the data storage 21. The stored exercise data can be used for all kinds of analysis at a later point in time. If a user device 40 is registered on a certain machine, then exercise data will be forwarded to the user device 50 in real-time. In other words, exercise data corresponding to every detected repetition will be forwarded to the user device 50.

The user device 50 is e.g. a smartphone comprising a mobile application, e.g. an android app. In the mobile application the user may monitor machine training automatically in real-time, follow pre-defined workouts or save your personal workouts, view history of all training data, workout programs, statistics and progress.

The user device 50 is configured to receive the near field wireless signal from the exercise machine identifier 40. The user device 50 is configured to communicate with the server 20 and to retrieve exercise data from the server 20. The user device 50 may also inform the server 20 that it intends to start training in an exercise machine 1. In other words, the user device 50 is configured to register (log-in)/de-register (log-off) itself at the exercise machine 1.

When a user device 50 is registered at the exercise machine 1, the server 20 will then start forwarding exercise data to the user device in real-time. In other words, the user device 50 is configured to retrieve, from the server 20, exercise data corresponding to an exercise machine identity comprised in the received near field wireless signal.

The user device 50 will present exercise data (or information associated therewith) to the user in any form depending on implementation. For example, the weight, the number of repetitions and the exercise machine's name are displayed on a display of the user device 50. In other words, the user device 50 is configured to provide the retrieved exercise data to a user. After completion of the exercising the entire program is typically sent to the server 20 for storage.

In this example the observer, the user device 50 and the server 20 would together constitute the control arrangement 200*a* of the exercise monitoring system 100*a*.

FIG. 8*e* illustrates an example user interface projected on the user device 50. The user interface illustrates the number of repetitions 51 in real-time and also the number of sets performed 52. The user interface also shows the name 53 of the exercise machine 1 to which the user is logged in.

FIG. 8*f* illustrates the holder 70. The holder 70 is configured to be arranged at an exercise machine to hold a user device during exercise. The holder comprises a sensor 71 and a short range communication interface 72. The holder corresponds to the holder described in FIG. 2.

Figure 9:
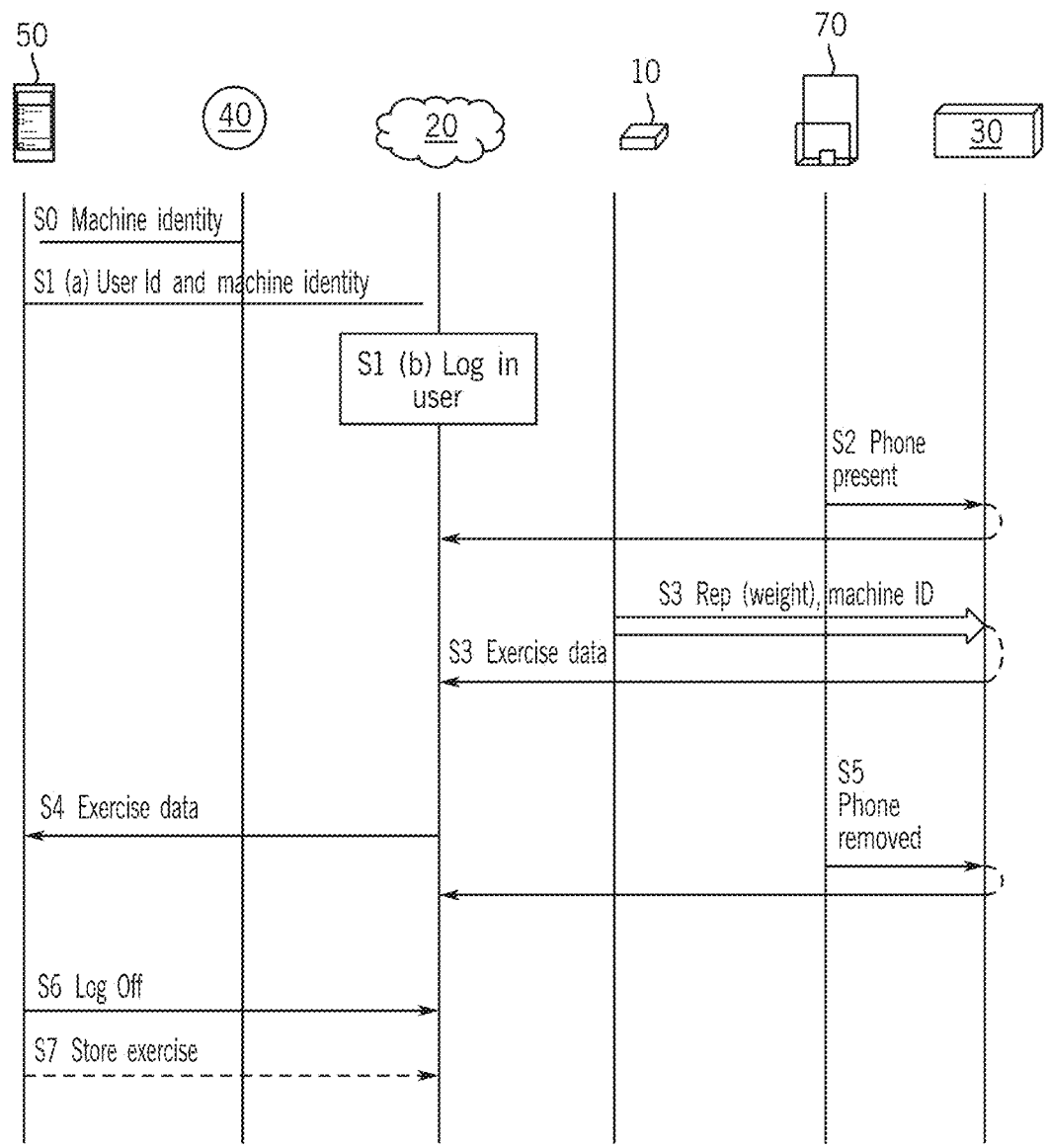
FIG. 9 illustrates signaling between the devices in the monitoring system in the system of FIG. 7.

FIG. 9 illustrates the signaling between the devices in the exercise monitoring system 100*a* when using the proposed solution in the exercise machine monitoring system of FIG. 7.

The method is started when a user touches ("blips") his/her user device 50 at the exercise machine identifier 40, and is detected by the proximity sensor on the exercise machine identifier 40.

S0) The exercise machine identifier 40 then sends the exercise machine identity to the user device 50 with BLE. The exercise machine identifier 40 transmits at minimum power, so it only reaches the user device 50, which is close by.

S1) The user id that the user is logged in with, is sent (step a) to the server 20 together with the exercise machine identity. The user is now registered or logged in (step b) at the exercise machine 1.

The user then places the user device 50 in the holder 70, to get ready to start exercising (or training).

S2) The holder detects (S71 of FIG. 5) the presence and starts to broadcast (S72 of FIG. 5) the identity of the exercise machine and an indication that the object is placed in the holder 70 using BLE. The signal is fetched by the observer 30 and forwarded to the server 20, which registers the information that an object (assumed to be the user's phone) is placed in the holder 70. The observer will typically forward all signals detected to the server.

When the user starts a repetition (i.e. starts training), an accelerometer of the repetition detector 10 wakes up the repetition detector 10 from sleep mode. A sensor e.g. a Time of Flight sensor measures the distance to the top of the exercise machine. When the repetition detector is back to starting position for a few seconds it goes to sleep again.

When the cable which lifts the weight pack is stretched (this is a way to ensure consistency in measurements), the distance toward the pin may be measured with another time of flight sensor. This distance represents a weight.

S3) The observer broadcasts a short range wireless communication signal comprising machine ID and repetitions. The repetitions are sent (or broadcasted) constantly (i.e. in real-time, one by one) as they occur to the observer via BLE. The weight is only sent once to the observer 30 via BLE.

The observer 30 is positioned centrally in the gym, and there can be more than one observer 30 in a gym. The observers receive the packages from the exercise machine(s) in the gym. The observer 30 sends (or forwards) the received repetition information on to the server 20.

S4) The server 20 knows which user is exercising at which machine (due to registration (log-in) S1) and sends the repetitions and weight further to the user device 50 of the logged in user which presents it to the user (see FIG. 8*e*).

When the user has finished exercising the user removes his user device from the holder 70 and leaves the exercise machine 1.

S6) The holder detects (S73 of FIG. 5) the removal and starts to broadcast (S74 of FIG. 5) a signal comprising the identity of the exercise machine and an indication that the object is removed from the holder 70, using BLE. The signal is fetched by the observer and forwarded to the server 20. The server 20 receives the signal and checks which user is logged in at the machine identified by the signal, namely user device 50. The server 20 then tells the user device 50 to log off from the exercise machine 1, alternatively, the user is automatically logged out (and the user may then be notified).

S7) The entire exercise is stored in the server 20 or in a data storage, once the set or the entire exercise is completed.

This example implementation solution is dependent upon a good internet, since the real-time experience is delivered over internet. With a local connectivity based solution it is possible get away from the problem. If the internet is lagging in the connection from the observer to the server in a cloud, or from the server in a cloud to the user device, the user experience will be bad.

Figure 10:
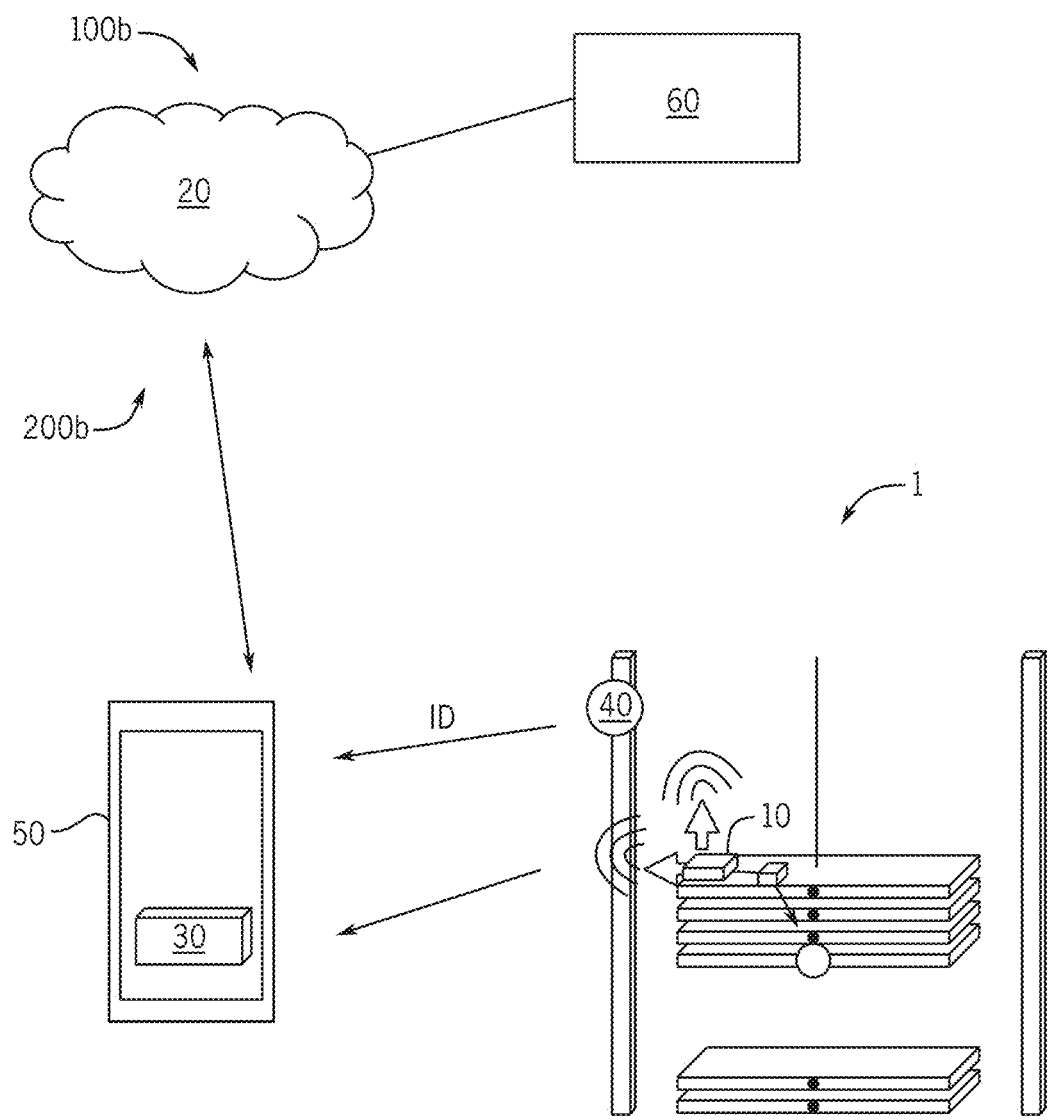
FIG. 10 illustrates another example exercise monitoring system.

FIG. 10 illustrates a second example implementation of the proposed technique. This embodiment differs from the first example embodiment in that the functionality of the observer 30 is at least partly integrated in the user device 50, e.g. the user's smartphone. This means that during exercise the signaling to from a server 20 over internet is not needed or at least not required, as all data may be stored in the user device 50 at least until the exercise is completed.

The repetition detector 10, the exercise machine identifier 40 will be the same as in the first example embodiment.

However, the functionality of the observer 30 and the user device 50 would typically be different, as no signaling there between is needed. In particular the repetition detector 10 will provide the exercise data directly to the user device 50, as the observer functionality is comprised therein.

Furthermore, the user device 50 will be configured to, when occupied, broadcast a signal that informs other user devices that the exercise machine 1 is occupied.

Figure 11:
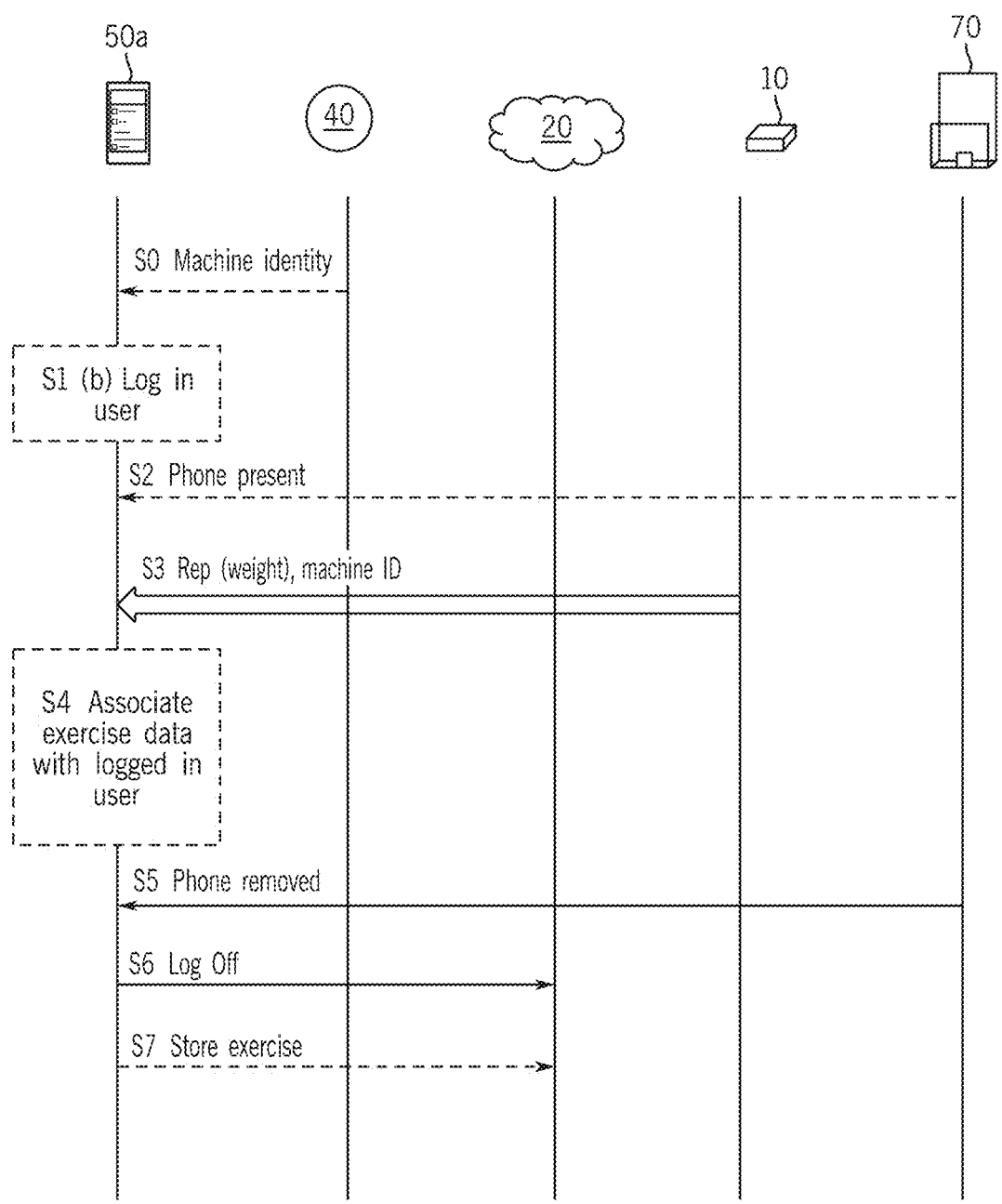
FIG. 11 illustrates signaling between the devices in the monitoring system in the system of FIG. 10.

FIG. 11 illustrates signaling between the devices in the monitoring system in the system of FIG. 10.

The method is initiated when the user device 50 touches the exercise machine identifier 40, and is detected by the proximity sensor on the exercise machine identifier 40.

S1) The exercise machine identifier 40 then sends the exercise machine identity of the exercise machine 1 with BLE to the user device 50. It transmits at minimum power, so it only reaches the user device 50 which is close by. It is received by the user device 50 or alternatively the user device 50 reads the id by NFC.

S2) The user device 50 starts to listen to the repetition detector 10 of the exercise machine 1 identified by the id. The user device 50 also broadcasts (not shown) to all other user devices a signal instructing them to stop listening to this machine (i.e. the exercise machine with the received the exercise machine identity).

As in the first example embodiment, the accelerometer of the repetition detector 10 wakes up the system from sleep mode, when the user starts a repetition. The Time of Flight sensor measures the distance to the top of the exercise machine. When the repetition detector 10 is back to starting position for a few seconds it goes to sleep again. When the cable which lifts the weight pack is stretched (this is a way to ensure consistency in measurements) the distance toward the pin is measured with another time of flight sensor. This distance represents a weight.

S3) As in the previous example, the repetition detector 10 continuously broadcasts detected repetitions (i.e. in real-time) via BLE. The weight is sent once via BLE. The user device 50 which listens to the exercise machine receives the detection and weight information and presents it to the user. In other words, the user device 40 monitors/scans for a short-range wireless communication signal comprising the exercise machine ID received in step S1. In other words, the short range wireless signal is monitored directly by the observer 30 comprised in the user device 50.

S4) The user device associates the received exercise data with the user being logged in at the exercise machine 1.

When the user finished his exercise he or she takes his user device and moves on to another machine. The sensor of the holder 70 will detect (S73 of FIG. 5) that an object assumed to be the user device 50 is removed and then broadcasts (S74 of FIG. 5) a BLE signal indicating that that an object is removed from the holder 70.

S5) The user device 50 receives the broadcasted signal.

S6) The received broadcasted signal serves as an indication for the user device to log off the exercise machine 1. The first user may be automatically logged off or may be prompted to log off. The user device may also broadcast a signal indicating that it is logged off. This signal may be fetched by other user devices in the gym.

S7) The user device 50 can backup or store the exercise in the remote data storage 21, but is not necessary. The monitoring system 100b can run without a data storage or data may be uploaded at a later point in time, when connection has been established.

In the drawings and specification, there have been disclosed exemplary aspects of the disclosure. However, many variations and modifications can be made to these aspects without substantially departing from the principles of the present disclosure. Thus, the disclosure should be regarded as illustrative rather than restrictive, and not as being limited to the particular aspects discussed above.

Accordingly, although specific terms are employed, they are used in a generic and descriptive sense only and not for purposes of limitation.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, apparatus, modules, systems, and computer program products. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be implemented at least in part by means of both hardware and software, and that several "means", "units" or "devices" may be represented by the same item of hardware.

The various example embodiments described herein are described in the general context of method steps or processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that performs particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

The invention claimed is:

1. A method for logging out a user from an exercise machine via a user device, the method comprising:
receiving via the user device a machine identity of the exercise machine, wherein the user device is associated with the user and separable from the exercise machine;

receiving from the user device, other than by the exercise machine, both a user identity associated with the user device and the machine identity of the exercise machine;

logging in the user at the exercise machine with the user identity and the machine identity;

receiving exercise data associated with exercise performed at the exercise machine;

associating the received exercise data with the logged-in user;

receiving, from a holder arranged at the exercise machine, a preceding signal indicating the machine identity of the exercise machine and an indication that an object has been placed in the holder;

receiving, from the holder arranged at the exercise machine, a wireless signal indicating said machine identity of the exercise machine and an indication that the object has been removed from the holder; and logging out the user from the exercise machine in response to receiving the signal.

2. The method of claim 1, further comprising indicating logging in the user at the exercise machine.

3. The method of claim 1, wherein the machine identity of the exercise machine is received via the user device via a near-field wireless signal.

4. The method of claim 1, wherein the method is performed in parallel for a plurality of exercise machines.

5. The method of claim 1, wherein the holder is configured to hold the user device of the user during exercise.

6. The method of claim 1, wherein the object removed from the holder is an object other than the user device.

7. A control arrangement comprising:

a communication interface configured to enable communication with a plurality of exercise machines each provided with a holder; and processing circuitry configured to:

receive, from one of the exercise machines, exercise data associated with exercise performed at the exercise machine;

associate the received exercise data with a user being logged in at the exercise machine;

receive a machine identity of the exercise machine;

receive, from the holder, a preceding signal indicating the machine identity of the exercise machine and an indication that a first object has been placed in the holder;

receive, from the holder of the exercise machine, an indication that the first object is removed from the holder; and log out the user from the exercise machine in response to receiving the indication that the first object was removed from the holder, wherein the processing circuitry is further configured to receive the machine identity from the first object that is separable from the exercise machine and/or to receive a user identity for logging in the user from a second object that is separable from the exercise machine and different from the first object, the exercise machine being operable without the second object being in the holder.

8. The control arrangement of claim 7, wherein the processing circuitry is further configured to:

log in a user at the exercise machine in response to receiving a near-field wireless signal indicating the machine identity.

9. The control arrangement of claim 7, wherein the processing circuitry is further configured to:

receive, from the holder, a preceding signal indicating the machine identity and an indication that the first object is placed in the holder.

\* \* \* \* \*